United States Patent
Igarashi et al.

(10) Patent No.: US 9,972,084 B2
(45) Date of Patent: May 15, 2018

(54) MEDICAL IMAGE PROCESSING APPARATUS AND IMAGE DISPLAY CONTROL METHOD FOR THE SAME

(71) Applicant: TOSHIBA MEDICAL SYSTEMS CORPORATION, Otawara-Shi (JP)

(72) Inventors: Takuma Igarashi, Nasushiobara (JP); Tatsuya Kimoto, Utsunomiya (JP); Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 94 days.

(21) Appl. No.: 15/089,670

(22) Filed: Apr. 4, 2016

(65) Prior Publication Data

US 2016/0350911 A1 Dec. 1, 2016

(30) Foreign Application Priority Data

Jun. 1, 2015 (JP) .................................. 2015-111545

(51) Int. Cl.
| | |
|---|---|
| *G06K 9/00* | (2006.01) |
| *G06T 7/00* | (2017.01) |
| *A61B 6/00* | (2006.01) |
| *G06T 11/60* | (2006.01) |
| *A61B 6/03* | (2006.01) |

(52) U.S. Cl.
CPC .............. *G06T 7/0012* (2013.01); *A61B 6/50* (2013.01); *A61B 6/5217* (2013.01); *G06T 11/60* (2013.01); *A61B 6/032* (2013.01); *G06T 2207/10081* (2013.01); *G06T 2207/30061* (2013.01)

(58) Field of Classification Search
None
See application file for complete search history.

(56) References Cited

U.S. PATENT DOCUMENTS

| | | | | |
|---|---|---|---|---|
| 2003/0219496 | A1* | 11/2003 | Otterbein | A61K 33/00 424/699 |
| 2008/0298658 | A1* | 12/2008 | Nakashima | A61B 5/055 382/131 |
| 2013/0315455 | A1* | 11/2013 | Wakai | A61B 6/5211 382/128 |

FOREIGN PATENT DOCUMENTS

JP 2014-236862 12/2014

OTHER PUBLICATIONS

Visualization of complete regression of pulmonary arterial remodeling on optical coherence tomography in a patient with pulmonary arterial hypertension, by Dai et al, Department of cardiovascular medicine, Tohoku University Graduate school of medicine, Sendai, Japan, official journal of the Japanese circulation society (hereinafter Dai), Jul. 9, 2014.*

(Continued)

*Primary Examiner* — Vikkram Bali
(74) *Attorney, Agent, or Firm* — Oblon, McClelland, Maier & Neustadt, L.L.P.

(57) ABSTRACT

A medical image processing apparatus according to the embodiments includes a display, and processing circuitry configured to execute a program. The processing circuitry extracts at least part of a lung from three-dimensional image data, extracts a tubular structure from at least part of the extracted lung, calculates area ratios between a lumen and a wall of the extracted tubular structure along the tubular structure, and generates area ratio images by allocating pixel values, corresponding to the calculated area ratios, to corresponding positions on the tubular structure having the area ratios being calculated, and displays the area ratio images on the display.

9 Claims, 11 Drawing Sheets

(56) References Cited

OTHER PUBLICATIONS

Optical coherence tomography of the pulmonary arteries: A systematic review, by Jorge et al., Department of cardiology, Journal of Cardiology 67 (2013) 6-14.*
"Read three-dimensional diagnostic images in combination with a PACS and a report system, and use it for explaining the diagnosis result to a patient" http://www.innervision.co.jp/suite_ws/ziosoft/1111/, New Horizon of 4D imaging, vol. 11, 2016, 6 pages (with English translation).
"Lumen Diameter", Booklet from Coreline Soft, 2 pages.

* cited by examiner

MEDICAL IMAGE PROCESSING APPARATUS AND IMAGE DISPLAY CONTROL METHOD FOR THE SAME

CROSS-REFERENCE TO RELATED APPLICATION

This application is based upon and claims the benefit of priority from Japanese Patent Application No. 2015-111545, filed on Jun. 1, 2015, the entire contents of which are incorporated herein by reference.

FIELD

The present embodiment as one aspect of the present invention relates to a medical image processing apparatus and an image display control method for the same.

BACKGROUND

Chronic obstructive pulmonary disease (COPD) is known to include emphysema predominant COPD and airway disease predominant COPD. In the case of emphysema predominant COPD, lung tissue is broken down by toxic substances for example, and the resultant reduction in alveoli leads to reduction in the force of supporting bronchi, which makes it difficult to expand the bronchi. In the case of airway disease predominant COPD, some of the bronchi are narrowed by factors other than emphysema, which results in airflow obstruction.

In the case of emphysema predominant COPD, an emphysematous lesion is extracted as a low attenuation area (LAA) with high-resolution (HR) computed tomography (CT). A ratio of the low attenuation area to an entire lung determines advance degree and severity of the emphysema.

On the contrary, since airway disease predominant COPD involves thickened airway walls and narrowed lumens, axial images are used for diagnosis, so that states of airways are visually observed by an operator.

In this connection, for example, a medical image processing apparatus is being examined which is configured to generate a curved multi-planar reconstruction image including images of many abnormal spots.

It is also being examined to visually observe a large number of cross sections of a bronchus and to numerically calculate and display a cross-sectional area for the purpose of bronchial analysis.

However, in the case of, for example, calculating cross sections of a bronchial outer wall and a bronchial inner wall and calculating area ratios therebetween to perform diagnostic reading of the cross sections with axial images, the area ratios are presented only in the form of numerical values. Accordingly, when one area ratio is displayed on a certain image, it is impossible to identify which location the displayed area ratio relates to in the entire image. Moreover, when diagnostic reading is performed with axial images, bronchi are displayed as tubular structures equivalent to blood vessels, which makes it difficult to instantaneously discriminate a bronchus that is a target of diagnostic reading.

BRIEF DESCRIPTION OF THE DRAWINGS

In accompanying drawings.

DETAILED DESCRIPTION

A medical image processing apparatus according to the present embodiment includes: a display; and a processing circuitry configured to execute program, wherein the processing circuitry extracts at least part of a lung from three-dimensional image data, extracts a tubular structure from at least part of the extracted lung, calculates area ratios between a lumen and a wall of the extracted tubular structure along the extracted tubular structure; and generates area ratio images by allocating pixel values, corresponding to the calculated area ratios, to corresponding positions on the tubular structure having the area ratios being calculated, and displays the area ratio images on the display.

First Embodiment

A medical image processing apparatus and an image display control method for the same according to the present embodiment will be described with reference to the accompanying drawings.

Figure 1:
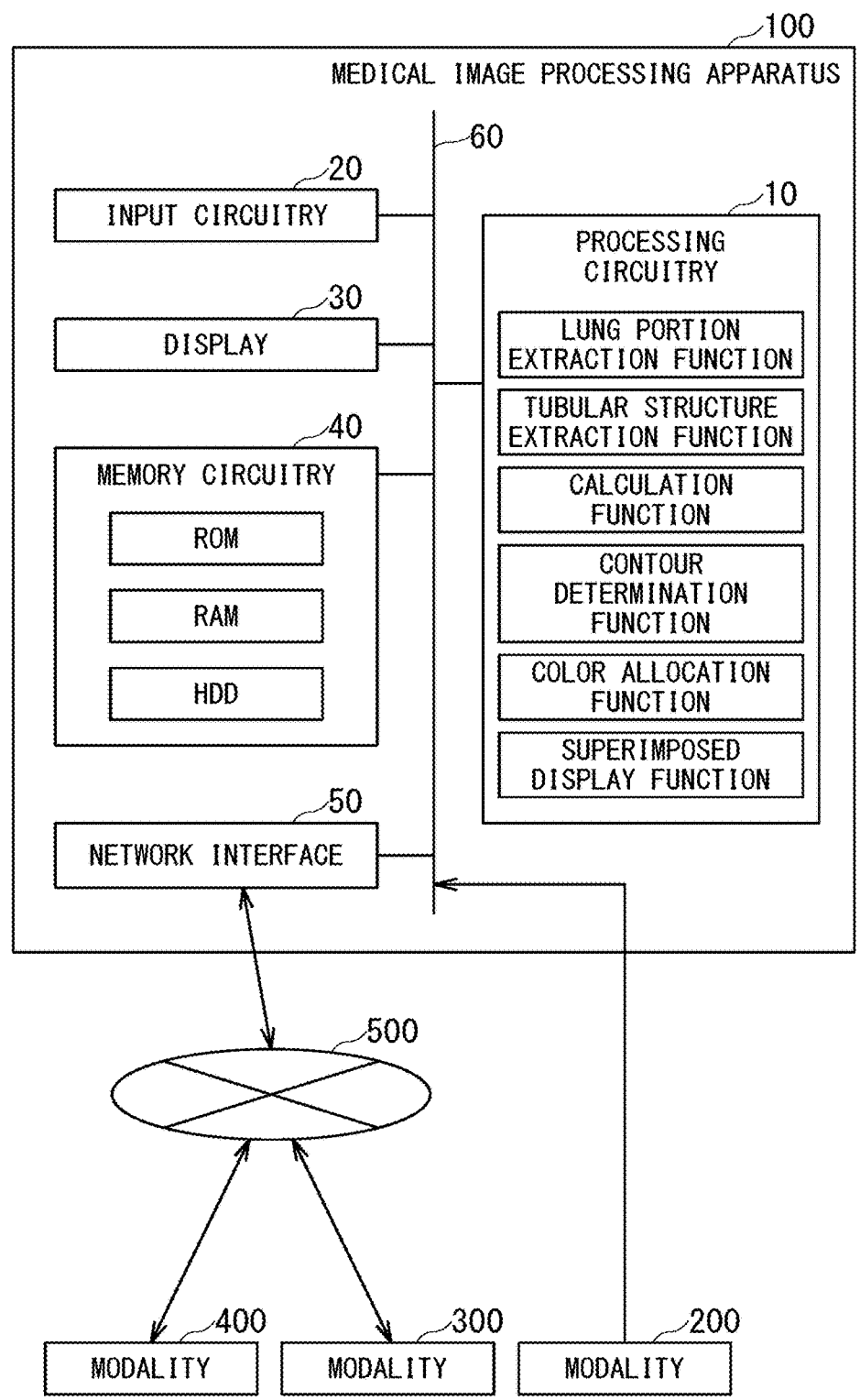
FIG. 1 is a block diagram illustrating one configuration example of a medical image processing apparatus in the present embodiment.

FIG. 1 is a block diagram illustrating one configuration example of a medical image processing apparatus 100 in the present embodiment.

As illustrated in FIG. 1, the medical image processing apparatus 100 according to the present embodiment includes a processing circuitry 10, an input circuitry 20, a display 30, a memory circuitry 40, a network interface 50, and an internal bus 60.

The processing circuitry 10 of the medical image processing apparatus 100 is a processor which reads programs from a memory (memory circuitry 40) and executes the programs to implement functions corresponding to the programs. In other words, the processing circuitry 10 includes a processor, which executes programs to implement a lung portion extraction function, a tubular structure extraction function, a contour determination function, a calculation function, a color allocation function, and a superimposed display function illustrated in FIG. 1.

The lung portion extraction function is performed by the processing circuitry 10 to extract at least part of a lung from three-dimensional image data. For example, the processing circuitry 10 extracts at least part of the lung from three-dimensional image data based on pixel values (for example, CT values) of the three-dimensional image data (volume data). The lung may be extracted partially or entirely.

The tubular structure extraction function is performed by the processing circuitry 10 to extract a tubular structure from at least part of the extracted lung. For example, the processing circuitry 10 extracts a tubular structure from at least part of the lung portion extracted from the three-dimensional image data. Although a bronchus is used as one example of a tubular structure in a description of the present embodiment, the tubular structure is not limited thereto.

The contour determination function is performed by the processing circuitry 10 to determine contours of an inner wall and an outer wall of the extracted tubular structure along a core line of the tubular structure.

The calculation function is performed by the processing circuitry 10 to calculate area ratios between a lumen and a wall of the extracted tubular structure along the tubular structure based on the contours of the inner wall and the outer wall determined by the contour determination function. Alternatively, the calculation function may be performed by the processing circuitry 10, based on the contours of the inner wall and the outer wall determined by the contour determination function, to calculate area ratios between a cross-sectional area of the tubular structure (i.e., an area inside the contour of the outer wall of the tubular structure) and a cross-sectional area of the wall (i.e., an area obtained by excluding an area inside the contour of the inner wall from the area inside the contour of the outer wall) along the extracted tubular structure.

The color allocation function is performed by the processing circuitry 10 to allocate pixel values corresponding to the calculated area ratios to the tubular structure in three-dimensional image data to generate area ratio images. For example, the processing circuitry 10 allocates colors corresponding to the area ratios calculated by the calculation function to corresponding positions on the tubular structure having the area ratios being calculated to generate area ratio images.

The pixel values allocated by the color allocation function, or the pixel values in the area ratio images, are color information values of respective pixels. For example, color allocation is performed by color mapping using the pixel values. The pixel values may be color information values which include not only chromatic color information but also achromatic color information (i.e., gray scale). The pixel values may be transparent, and may further include a pattern and texture. The texture is defined as a texture of a surface of an image which is pseudo-expressed by using visual light and darkness.

The area ratio image is defined as an image generated by using the color allocation function which allocates a pixel value corresponding to an area ratio to a corresponding position on a tubular structure in three-dimensional image data.

The superimposed display control function is performed by the processing circuitry 10 to display pixel values corresponding to the area ratios calculated by the calculation function in a superimposed manner on the tubular structure. For example, the processing circuitry 10 displays a tubular structure on the display 30, while displaying colors corresponding to the area ratios in a superimposed manner on the tubular structure. In this case, the processing circuitry 10 can display the area ratio images superimposed on the displayed tubular structure.

A term "processor" used in the above description refers to a circuitry such as a dedicated or general-purpose central processing unit (CPU) or graphics processing unit (GPU), or an application-specific integrated circuit (ASIC), a programmable logic device (for example, a simple programmable logic device (SPLD), a complex programmable logic device (CPLD), and a field programmable gate array (FPGA)). Although FIG. 1 illustrates a case where one processor (processing circuitry 10) is provided, two or more processors may be provided.

The processor implements various functions by reading and executing programs which are stored in a memory or directly installed in a circuitry inside the processor. When a plurality of processors are provided, each processor may include a memory that stores the programs. Or the memory circuitry 40 of FIG. 1 may store the programs corresponding to the functions of the respective processors.

The input circuitry 20 is a pointing device operable by an operator. An input signal in conformity to an operation is sent to the processing circuitry 10.

The display 30 includes an image synthesis circuitry, a video random access memory (VRAM), and a display, which are not illustrated. The image synthesis circuitry generates synthesis data generated by synthesizing image data with text data of various parameters or the like. The VRAM expands the synthesis data on the display. The display 30 is constituted by a liquid crystal display, a cathode ray tube (CRT), or the like, to display images.

The memory circuitry 40 constituting the memory is a storage device including a read only memory (ROM), a random access memory (RAM), and a hard disk drive (HDD). The memory circuitry 40 stores an initial program loading (IPL), a basic input/output system (BIOS) and data, and is also used as a work memory or a temporal storage of data of the processing circuitry 10. The HDD is a storage device that stores programs (including application programs and an operating system (OS)) installed in the medical image processing apparatus 100 and data. The HDD also enables the OS to provide a graphical user interface (GUI) which allows heavy use of graphics to display information for an operator such as a surgical operator on the display 30 and allows basic operations to be performed with the input circuitry 20.

The network interface 50 performs communication control in conformity to a prescribed protocol to connect to a network 500 through a telephone line, for example. Through the network interface 50, the medical image processing apparatus 100 is connected to the network 500, such as a local area network (LAN) and the Internet.

Modalities 200 to 400 are medical diagnostic imaging apparatuses, such as X-ray computed tomography (CT) apparatuses, magnetic resonance imaging (MRI) apparatuses, ultrasonic diagnostic apparatuses, and X-ray diagnostic apparatuses. By imaging an object with such modalities, three-dimensional image data (volume data) on the object can be generated.

The medical image processing apparatus 100 is connected to the modality 200 through the internal bus 60. The medical image processing apparatus 100 is connected to the modality 300 or the modality 400 through the network 500. The medical image processing apparatus 100 acquires reconstructed images and/or three-dimensional image data (volume data) from the modality 200 and stores them in the memory circuitry 40. The medical image processing apparatus 100 also receives reconstructed images and/or three-dimensional image data (volume data) from the modality 300 or the modality 400 through the network 500, and stores them in the memory circuitry 40.

(Area Ratio Display Processing)

A description is now given of one example of operation of the processing circuitry 10 in the medical image processing apparatus 100 according to the present embodiment.

Figure 2:
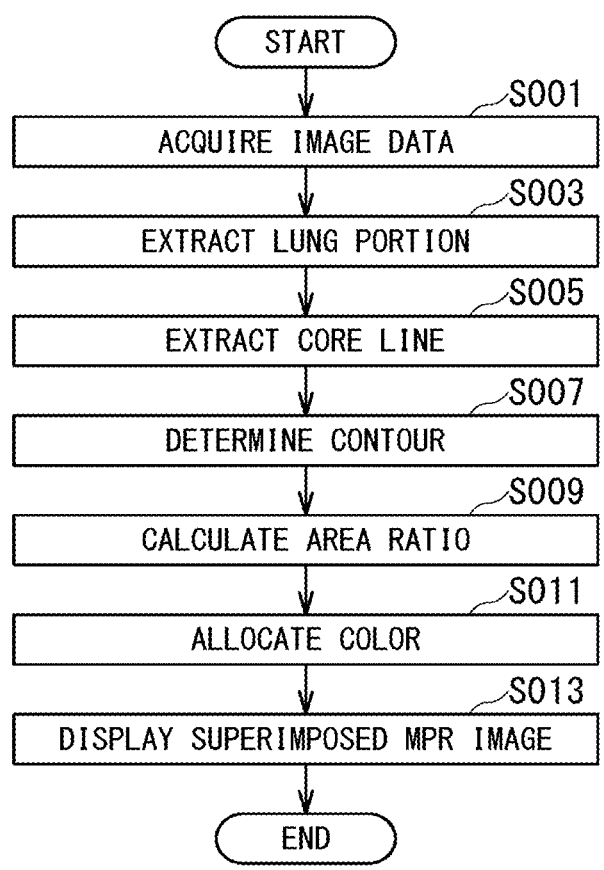
FIG. 2 is a flowchart illustrating procedures of area ratio display processing performed to display area ratios of a bronchus on an image of a lung portion by a processor of a processing circuitry of the medical image processing apparatus according to the present embodiment.

FIG. 2 is a flowchart illustrating procedures of the area ratio display processing performed to display area ratios of a bronchus on an image of a lung portion by a processor of the processing circuitry 10 in the medical image processing apparatus 100 according to the present embodiment. In FIG. 2, reference numerals with a character S attached thereto refer to steps of the flow chart.

First, in step S001, the processing circuitry 10 acquires three-dimensional image data (volume data) generated by the modality 200, and stores it in the memory circuitry 40. The processing circuitry 10 may receive three-dimensional image data (volume data) generated by the modality 300, the modality 400, or the like through the network 500 or the network interface 50, and stores it in the memory circuitry 40.

Next, in step S003, the processing circuitry 10 reads the three-dimensional image data from the memory circuitry 40, and extracts at least part of a lung from the three-dimensional image data based on pixel values of the three-dimensional image data. In this case, the processing circuitry 10 may extract part of the lung or the entire lung.

Next, in step S005, the processing circuitry 10 extracts a tubular structure from part of the lung portion extracted from the three-dimensional image data. Then, the processing circuitry 10 extracts a core line of the tubular structure. In this case, the processing circuitry 10 performs threshold processing of the three-dimensional image data so as to extract the core line of the tubular structure included in the three-dimensional image data through fully-automatic operation, manual operation, or semiautomatic operation.

For example, the processing circuitry 10 can extract the core line by extracting a region of the tubular structure and performing thinning of the region.

Next, in step S007, the processing circuitry 10 determines contours of an inner wall and an outer wall of the tubular structure extracted from the lung portion along the core line of the tubular structure. In this case, the processing circuitry 10 determines the contour of the inner wall and the contour of the outer wall by region growing along the core line of the tubular structure. The region growing is a publicly known method of extracting a target contour. In this method, region growing is repeated to determine the contours of the inner wall and the outer wall.

Next, in step S009, the processing circuitry 10 calculates, based on the contours of the inner wall and the outer wall determined by the contour determination function, an area ratio (=B/A) between an area (A) inside the contour of the outer wall of the tubular structure and an area (B) obtained by excluding an area inside the contour of the inner wall from the area inside the contour of the outer wall. A method of obtaining the area ratio is now described with reference to FIG. 3.

Figure 3:
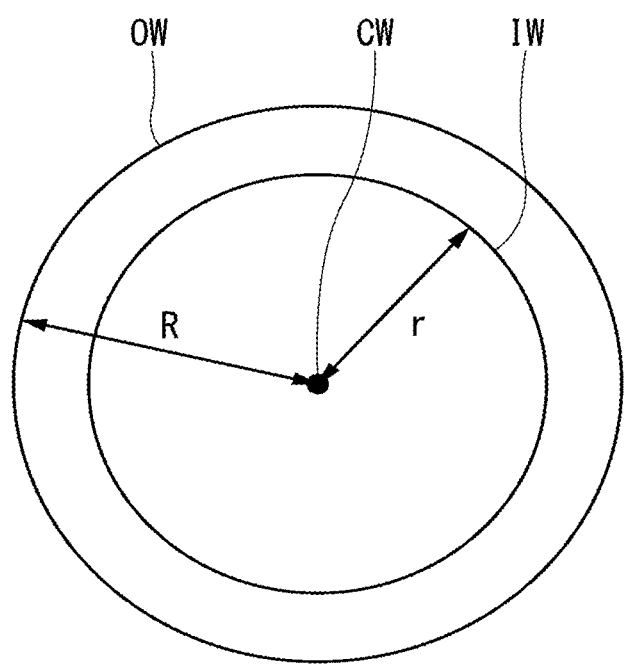
FIG. 3 is a concept view illustrating a calculation method of calculating area ratios by the processing circuitry of the medical image processing apparatus according to the present embodiment.

FIG. 3 is a concept view illustrating a calculation method of calculating an area ratio by the processing circuitry 10 in the medical image processing apparatus 100 according to the present embodiment.

As illustrated in FIG. 3, the processing circuitry 10 calculates the area ratio of a cross section of a bronchus representing a tubular structure. FIG. 3 includes a central axis CW of a tubular structure, an outer wall OW of the tubular structure, a radius R of the outer wall, an inner wall IW of the tubular structure, and a radius r of the inner wall. In this drawing, an area ratio (%) of a bronchus, which is a tubular structure, is expressed by Expression (1):

$$\text{Area ratio } W_A = (\pi(R^2 - r^2)/\pi R^2) \times 100 \quad (1)$$
$$= (1 - r^2/R^2) \times 100$$

Expression (1) is for obtaining the area ratio $W_A$ between an area $(\pi R^2)$ inside the contour of the outer wall of the tubular structure and an area $(\pi(R^2-r^2))$ obtained by excluding an area inside the contour of the inner wall from the area inside the contour of the outer wall.

The area ratio may be an area ratio $W_D$ between an area $(\pi r^2)$ of a lumen of the tubular structure and an area $(\pi(R^2-r^2))$ of a wall (region surrounded with the outer wall OW and the inner wall IW). In this case, the area ratio $W_B$ is expressed by Expression (2):

$$\text{Area ratio } W_B = (\pi(R^2 - r^2)/\pi r^2) \times 100 \quad (2)$$
$$= (R^2/r^2 - 1) \times 100$$

Both Expression (1) and Expression (2) are on the assumption that the outer wall OW and the inner wall IW have circular cross-sections. However, even when they have cross-sections other than the circular shape, the area ratio $W_7$, and the area ratio $W_B$ can still be calculated with publicly known techniques.

When the cross-sectional area is assumed to be identical over the entire tubular structure (when the radius R of the outer wall OW is assumed to be identical), the area ratio $W_A$ and the area ratio $W_B$ each indicates a small value, as the wall of the tubular structure becomes thinner, i.e., as a cross-sectional area of the lumen of the tubular structure is closer to the cross-sectional area of the entire tubular structure.

Next, in step S011, the processing circuitry 10 allocates colors corresponding to the area ratios calculated by the calculation function to corresponding positions on the tubular structure in the three-dimensional image data. For example, an area ratio of 10(%) is defined as a reference value since bronchi is considered to be in a better condition as the area ratio is closer to 0(%). Accordingly, a color representing a lower risk (for example, blue) is allocated to a position on the tubular structure as the area ratio at the position is below 10(%) and closer to 0(%). Meanwhile, as the area ratio is above 0(%) and farther from 10(%), a color representing a higher risk (for example, red) is allocated to the position. The values representing the area ratios are merely illustrative. For example, the area ratios may be divided in stages, and colors may be allocated in stages.

Figure 4:
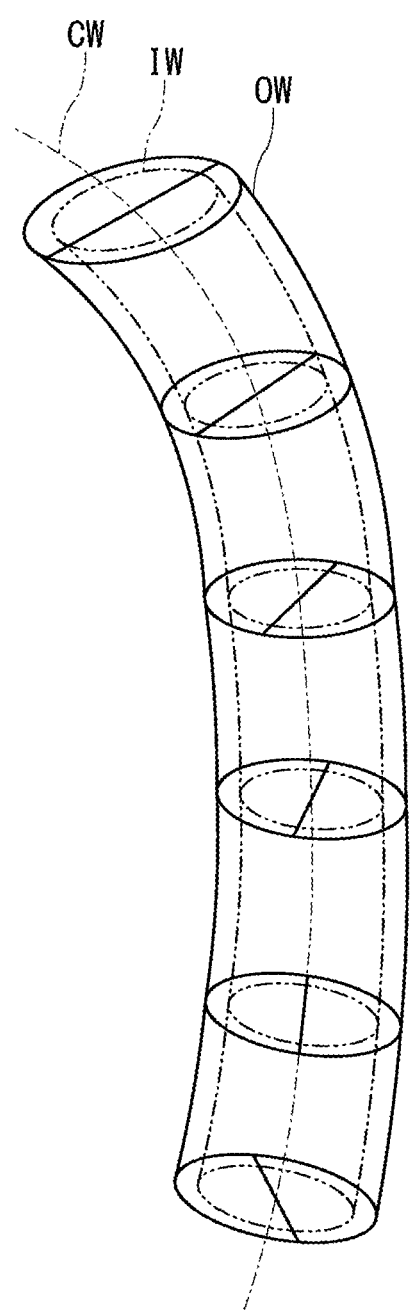
FIG. 4 is a concept view illustrating a concept in a case where the processing circuitry of the medical image processing apparatus according to the present embodiment allocates colors corresponding to the area ratios to corresponding positions of a tubular structure in three-dimensional image data.

FIG. 4 is a concept view illustrating a concept in a case where the processing circuitry 10 in the medical image processing apparatus 100 according to the present embodiment allocates colors corresponding to the area ratios to corresponding positions on the tubular structure in three-dimensional image data.

As illustrated in FIG. 4, the processing circuitry 10 divides a bronchus representing a tubular structure into cross sections, for example, at prescribed regular intervals along the central axis CW of the bronchus, and allocates a color to each cross section, the color corresponding to the area ratio of each cross section. Color allocation is not limited to allocation at prescribed interval. For example, colors may be allocated on the basis of microscopic displacement of volume (or capacity) corresponding to the cross section of the central axis CW. A color allocation range (an axial range of the tubular structure) is defined as a range in which the processing circuitry 10 extracts a core line of the tubular structure with the tubular structure extraction function.

Next, in step S013, the processing circuitry 10 displays the colors allocated in step S011 in a superimposed manner on the tubular structure on the image representing the three-dimensional image data. In this case, the display 30 displays the colors, which are allocated to the tubular structure on the image, to corresponding positions of the tubular structure. That is, the processing circuitry 10 displays area ratio images in a superimposed manner on the tubular structure in the display 30. For example, the processing circuitry 10 displays the tubular structure and the area ratio images as a superimposed multi-planar reconstruction (MPR) image in the display 30.

Figure 5:
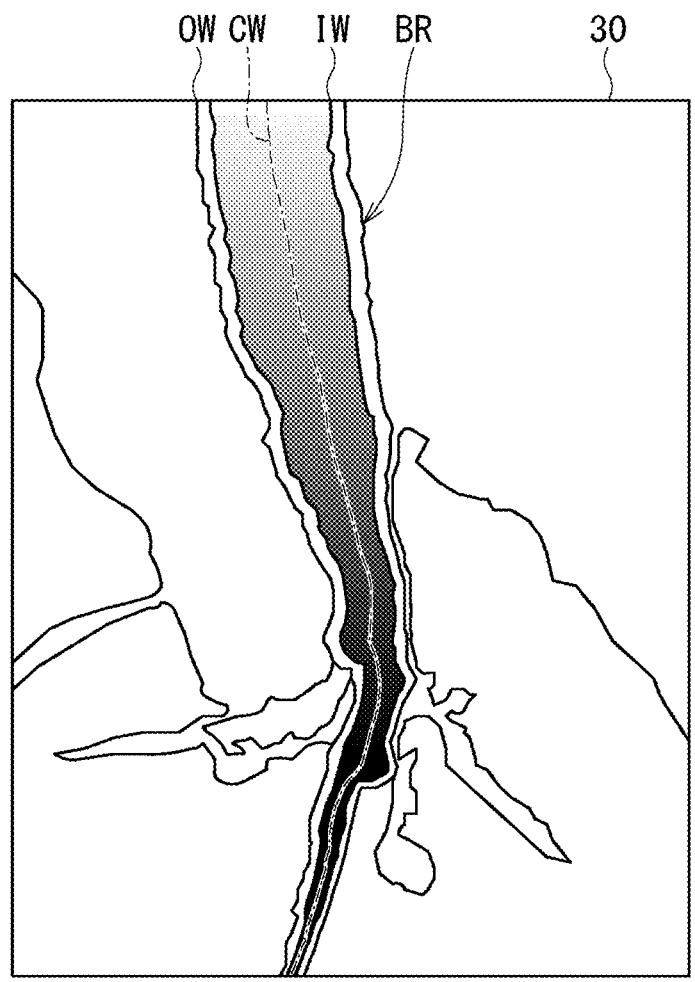
FIG. 5 is an image example when the processing circuitry of the medical image processing apparatus according to the present embodiment displays, on a display, area ratio images of a bronchus that is a tubular structure in a sagittal cross section in a superimposed manner on the bronchus by color mapping.

FIG. 5 is an image example when the processing circuitry 10 in the medical image processing apparatus 100 according to the present embodiment displays, on the display 30, area ratio images of a bronchus that is a tubular structure in a sagittal cross section in a superimposed manner on the bronchus by color mapping.

As illustrated in FIG. 5, in the display 30, regions of a bronchus BR having larger area ratios are displayed in red (higher density in FIG. 5), and regions of the bronchus BR having smaller area ratios are displayed in blue (lower density in FIG. 5).

Thus, the medical image processing apparatus 100 according to the present embodiment can present the area ratios of the entire tubular structure so that an operator such as a surgical operator easily and visually recognizes the area ratio. Since the tubular structure (bronchus) is colored according to the area ratio, the operator, such as a surgical operator, can immediately recognize regions which are larger and smaller in the area ratio.

Figure 6:
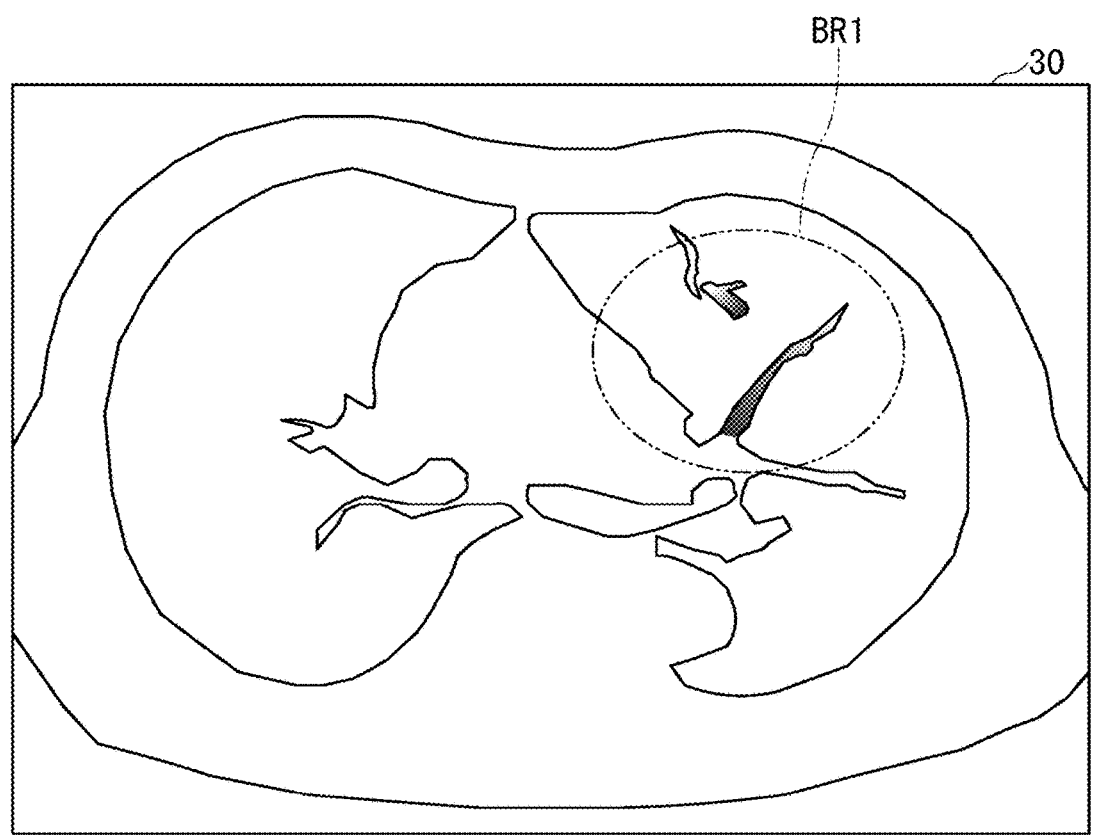
FIG. 6 is an image example when the processing circuitry of the medical image processing apparatus according to the present embodiment displays, on the display, area ratio images of a bronchus that is a tubular structure in an axial cross section in a superimposed manner on the bronchus by color mapping.

FIG. 6 is an image example when the processing circuitry 10 in the medical image processing apparatus 100 according to the present embodiment displays, on the display 30, area ratio images of a bronchus that is a tubular structure in an axial cross section in a superimposed manner on the bronchus by color mapping.

As illustrated in FIG. 6, a bronchus that is a tubular structure in the display 30 is displayed in a superimposed manner in color in a region BR1, which enables an existence position (existence location) of the bronchus to be recognized at a glance. Since the tubular structure is colored according to the area ratio, the operator, such as a surgical operator, can immediately recognize a spot of the tubular structure which is narrow in the cross section.

That is, since the area ratio images in color are displayed in a superimposed manner on the bronchus that is a tubular structure, the operator, such as a surgical operator, can easily recognize a spot of the tubular structure which is narrow in the cross section.

In step S013, the processing circuitry 10 displays, on the display 30, the area ratios of a bronchus that is a tubular structure in a superimposed manner on the bronchus by color mapping, and then ends the area ratio display processing.

As described in the foregoing, the medical image processing apparatus 100 according to the present embodiment makes the processing circuitry 10 extract part of the lung portion and also extract a tubular structure and a core line of the tubular structure. The medical image processing apparatus 100 according to the present embodiment makes the processing circuitry 10 determine the contours of an inner wall and an outer wall of the tubular structure along the core line of the tubular structure. Based on the contours of the inner wall and the outer wall, the processing circuitry 10 calculates area ratios between an area inside the contour of the outer wall of tubular structure and an area obtained by excluding an area inside the contour of the inner wall from the area inside the contour of the outer wall.

According to the present embodiment, the medical image processing apparatus 100 can make the processing circuitry 10 allocate pixel values corresponding to the area ratios to corresponding positions of the tubular structure in three-dimensional image data, and display the area ratio images in a superimposed manner on the tubular structure (for example, the bronchus) on the image representing the three-dimensional image data.

This enables the operator, such as a surgical operator, to detect at a glance where a tubular structure representing a bronchus is located on the image and to easily recognize the area ratios in the entire tubular structure on the image.

Although the processing circuitry 10 in the medical image processing apparatus 100 according to the present embodiment allocates colors corresponding to the area ratios to corresponding positions of the tubular structure in three-dimensional image data with the color allocation function, the present invention is not limited thereto.

For example, the processing circuitry 10 may allocate, as colors corresponding to the area ratios, gradient colors (gradation) to corresponding positions of the tubular structure in the three-dimensional image data with the color allocation function. As a result, the area ratio images in gradient colors (gradation) may be displayed in a superimposed manner on the tubular structure on the image representing the three-dimensional image data.

The processing circuitry 10 may display a core line of the tubular structure, which is displayed as a superimposed MPR image, as a cross-cut image on the display 30. For example, when a core line is selected with a mouse constituting the input circuitry 20 in the tubular structure displayed in FIGS. 5 and 6, the processing circuitry 10 may display, based on a position of the selected core line, a cross section inside the contour of the outer wall and inside the contour of the inner wall of the tubular structure which is orthogonal to the core line of the tubular structure on the display 30. In the present embodiment, a cross-cut image refers to a cross sectional image orthogonal to the core line of the tubular structure.

For example, in FIG. 5, when a specified position of the core line (i.e., the central axis CW) is selected in the bronchus BR representing a tubular structure, the processing circuitry 10 may display a cross-cut image of that position on the display 30.

Figure 7:
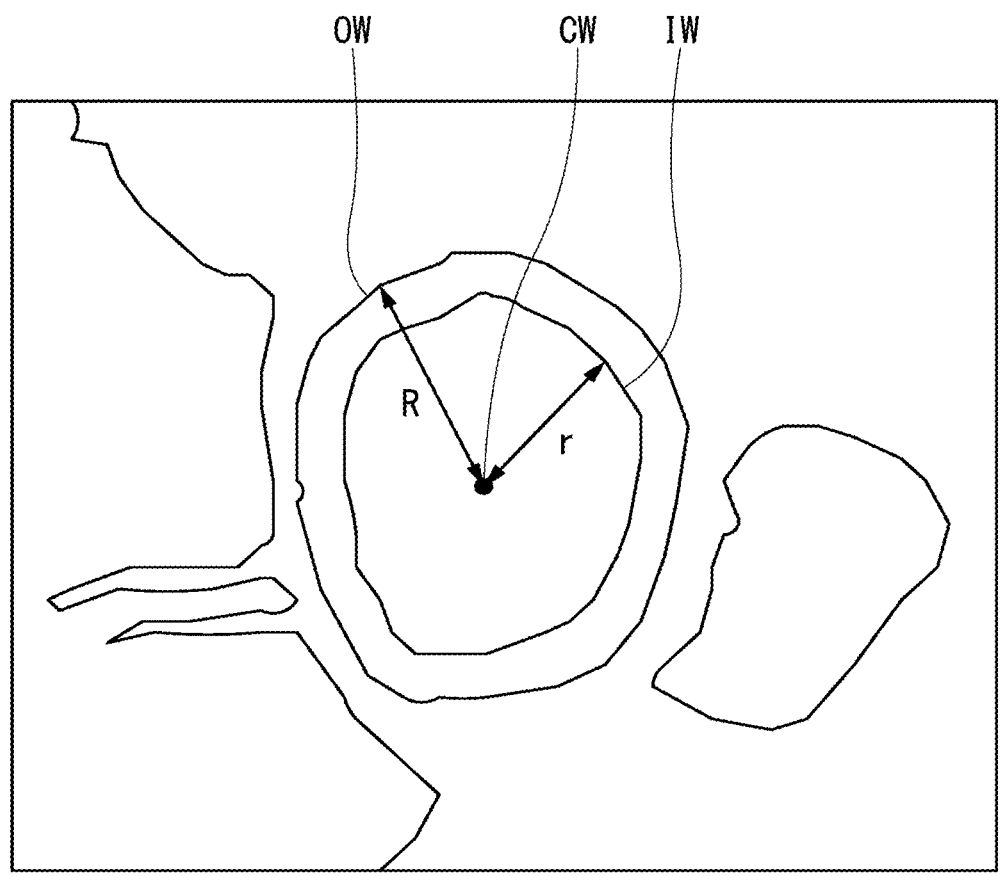
FIG. 7 is a display example in a case where a prescribed position of a core line is selected in a bronchus representing a tubular structure and the processing circuitry of the medical image processing apparatus according to the present embodiment displays on the display a cross-cut image of that position.

FIG. 7 is a display example in a case where a specified position of the core line is selected in the bronchus BR representing a tubular structure, and the processing circuitry 10 in the medical image processing apparatus 100 according to the present embodiment displays on the display 30 a cross-cut image of that position.

As illustrated in FIG. 7, a cross sectional image orthogonal to the core line (i.e., the central axis CW) of the bronchus BR representing a tubular structure is displayed on the display 30.

The processing circuitry 10 may also have a prescribed threshold corresponding to the calculated area ratio, and may preferentially display a position or a location of the tubular structure (bronchus) having the area ratio applicable to the threshold.

Although the processing circuitry 10 displays a bronchus that is a tubular structure and area ratio images superimposed in a sagittal cross section (FIG. 5) or an axial cross section (FIG. 6), the present invention is not limited thereto. For example, a cross section of an oblique image representing an arbitrary cross section may be generated, or images made by curved multi-planar reconstruction (CPR) and stretched CPR (SPR) may be displayed on the display 30.

The processing circuitry 10 may impart transparency to the colors allocated in the color allocation function so as to enable the operator, such as a surgical operator, to arbitrarily change a transparent degree while performing diagnostic reading of the tubular structure on the display 30.

Second Embodiment

In a second embodiment, the medical image processing apparatus 100 may further include an emphysema extraction function that extracts at least one emphysema region after part of the lung portion is extracted by the lung portion extraction function of the processing circuitry 10. In this case, the processing circuitry 10 extracts at least one emphysema region from the lung portion, and displays the emphysema region in association with a bronchus.

(Bronchial Region Display Processing Based on Emphysema Region)

Figure 8:
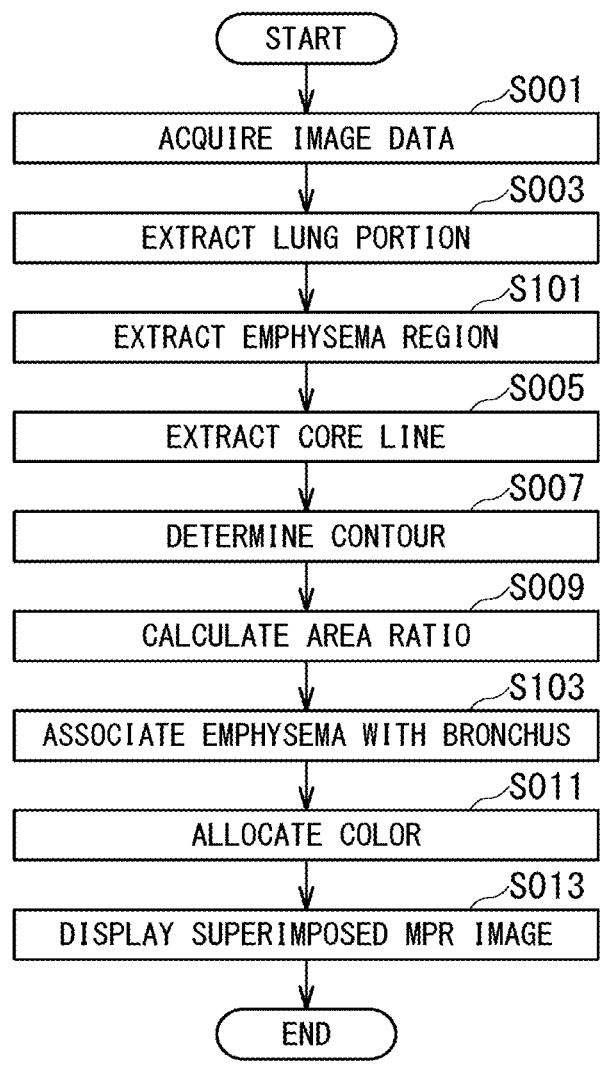
FIG. 8 is a flowchart illustrating procedures of bronchial region display processing performed to extract an emphysema region from a lung portion and to display a bronchus relating to the emphysema by the processor of the processing circuitry of the medical image processing apparatus according to the present embodiment.

FIG. 8 is a flowchart illustrating procedures of the bronchial region display processing performed to extract an emphysema region from a lung portion and to display a bronchus relating to emphysema by the processor of the processing circuitry 10 in the medical image processing apparatus 100 according to the present embodiment. In FIG. 8, reference numerals with a character S attached thereto refer to steps of the flow chart. Processes identical to those in FIG. 2 are designated by identical reference signs and descriptions thereof are omitted.

The flowchart of FIG. 8 is different from the flowchart of FIG. 2 in a point that steps S101 and S103 are added. Other processing aspects are identical.

In step S101, the processing circuitry 10 further extracts at least one region of emphysema (which is also simply called an emphysema region) from the lung portion extracted from three-dimensional image data in the tubular structure extraction function, for example. The extracted emphysema regions are clustered according to a distance from bronchi based on pixel values (for example, CT values).

In step S103, the processing circuitry 10 associates the area ratios of a tubular structure (bronchus), which were calculated by the contour determination function, with a bronchus positioned in a prescribed distance from the emphysema region. For example, the processing circuitry 10 associates all the bronchi positioned in a prescribed distance from the emphysema region as a related bronchus group.

As a result, in the second embodiment, the processing circuitry 10 can display area ratio images of one or more related bronchus groups (tubular structures) in the three-dimensional image data in the range of a prescribed distance from the extracted emphysema region in a superimposed manner on the related bronchus group or groups with the superimposed display function.

Figure 9:
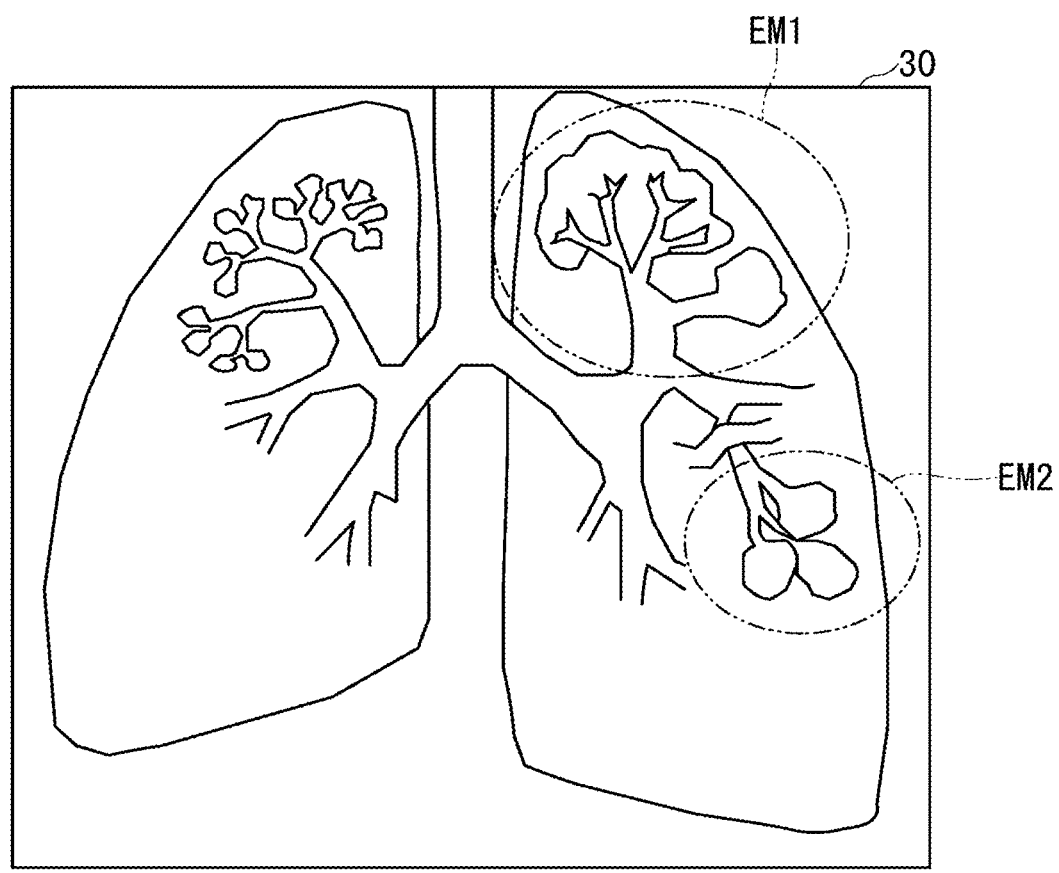
FIG. 9 is a concept view illustrating emphysema regions and related bronchus groups in a three-dimensional image data in a range of a prescribed distance, the emphysema regions being associated with the related bronchus groups by the processing circuitry of the medical image processing apparatus according to the present embodiment.

FIG. 9 is a concept view illustrating emphysema regions EM1 and EM 2 and related bronchus groups in three-dimensional image data within a prescribed distance, the emphysema regions being associated with the related bronchus groups by the processing circuitry 10 in the medical image processing apparatus 100 according to the present embodiment.

As illustrated in FIG. 9, a lung portion representing a three-dimensional image is displayed on the display 30. The emphysema regions EM1 and EM2 are displayed to represent emphysema regions. For example, it is assumed that the emphysema region EM1 is slightly larger than the emphysema region EM2, and is more advanced in disease stage than the emphysema region EM2.

For example, the processing circuitry 10 associates all the bronchi positioned in a prescribed distance from the emphysema region EM1 as the related bronchus group, and also associates all the bronchi positioned in a prescribed distance from the emphysema region EM2 as the related bronchus group.

As a result, the processing circuitry 10 can display area ratio images of the related bronchus groups in the range of a prescribed distance from the emphysema regions EM1 and EM2 in a superimposed manner on the related bronchus groups with the superimposed display function.

The processing circuitry 10 may extract an emphysema region larger than a prescribed size out of the emphysema regions. For example, since the emphysema region EM1 is slightly larger and more advanced in disease stage than the emphysema region EM2, it can be determined that the emphysema region EM1 is higher in disease severity. That is, the processing circuitry 10 can determine the severity based on the size of the emphysema regions. By allocating the severity to each prescribed size, the processing circuitry 10 can display area ratio images of a tubular structure which is within the range of a prescribed distance from the emphysema region, preferentially depending on the severity, in a superimposed manner on the tubular structure.

For example, the processing circuitry 10 are higher for emphysema region EM1 critical, the area ratio image related bronchus group from the emphysema area EM1 to a range of a predetermined distance, can be superimposed and displayed on its associated bronchial group.

Thus, in the case of the second embodiment, the processing circuitry 10 can display area ratio images of one or more tubular structures (related bronchus groups) in the three-dimensional image data in the range of a prescribed distance from the emphysema region in a superimposed manner on the tubular structures.

Figure 10:
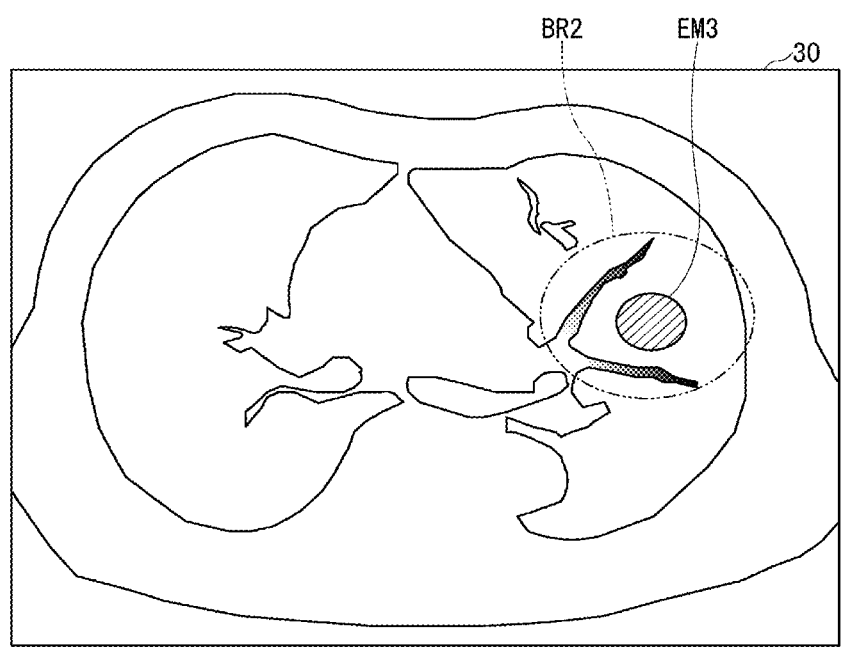
FIG. 10 is an image example when the processing circuitry of the medical image processing apparatus according to the present embodiment displays, on the display, an emphysema region and a related bronchus group in the range of a prescribed distance in an axial cross section by color mapping.

FIG. 10 is an image example when the processing circuitry 10 in the medical image processing apparatus 100 according to the present embodiment displays, on the display 30, an emphysema region EM3 and a related bronchus group BR2 in the range of a prescribed distance in an axial cross section by color mapping.

As illustrated in FIG. 10, the processing circuitry 10 displays, on the display 30, an area ratio image of the related bronchus group BR2, which is in the range of a prescribed distance from the emphysema region EM3, in a superimposed manner on the related bronchus group BR2. Although the emphysema region EM3 is displayed together with the related bronchus group BR2 in FIG. 10, the present invention is not limited thereto. That is, the emphysema region EM3 itself may be omitted in FIG. 10.

Figure 11:
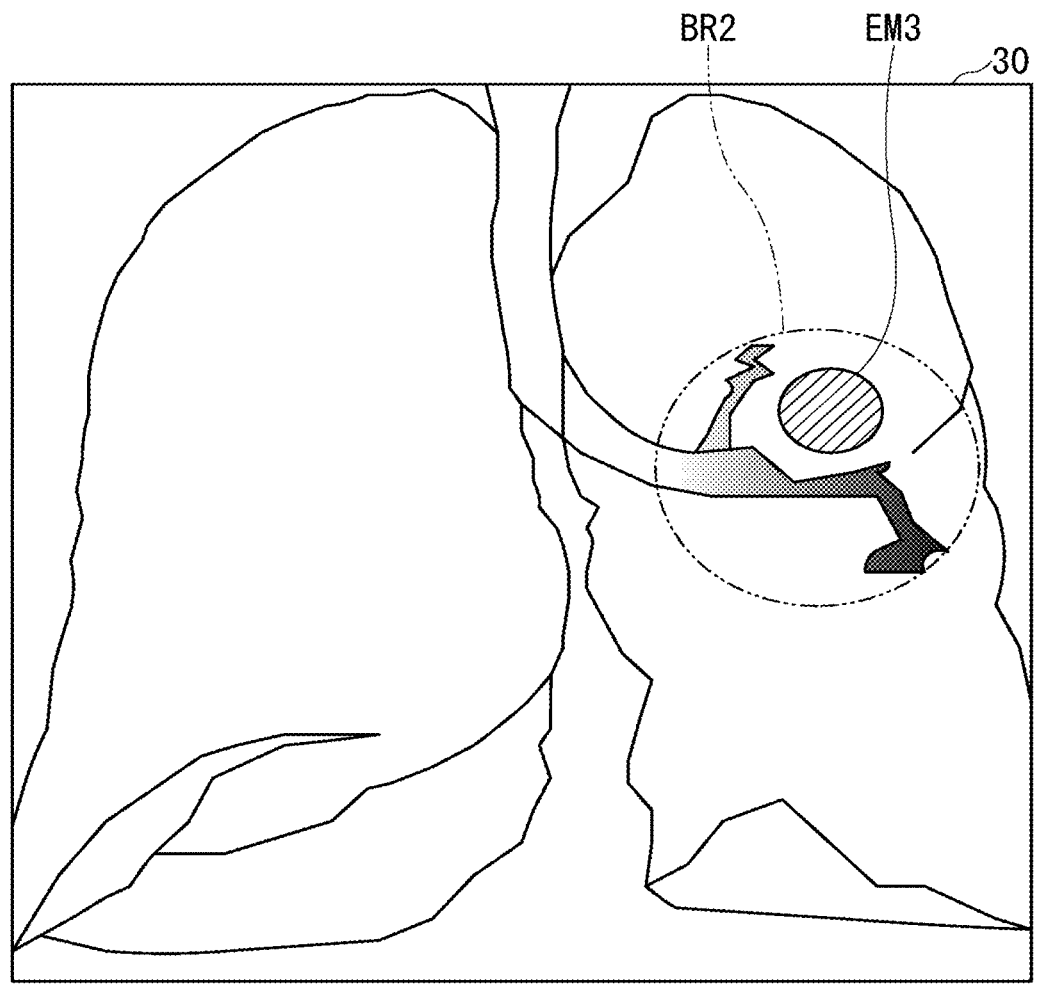
FIG. 11 is an image example when the processing circuitry of the medical image processing apparatus according to the present embodiment displays, on the display, the emphysema region and the related bronchus group in the range of a prescribed distance in a coronal cross section by color mapping.

FIG. 11 is an image example when the processing circuitry 10 in the medical image processing apparatus 100 according to the present embodiment displays, on the display 30, an area ratio image of the emphysema region EM3 and the related bronchus group BR2 in the range of a prescribed distance in a superimposed manner in a coronal cross section by color mapping.

As illustrated in FIG. 11, the processing circuitry 10 displays the area ratio images of the related bronchus group BR2, which is in the range of a prescribed distance from the emphysema region EM3, in a superimposed manner on the related bronchus group BR2 on the display 30. Although the emphysema region EM3 is displayed together with the related bronchus group BR2 in FIG. 11 as in FIG. 10, the present invention is not limited thereto. That is, the emphysema region EM3 itself may be omitted in FIG. 11.

As described in the foregoing, the medical image processing apparatus 100 according to the present embodiment can make the processing circuitry 10 further extract at least one emphysema region from the extracted lung portion and display the area ratio images of a related bronchus or bronchi (one or more tubular structures in three-dimensional image data) in the range of a prescribed distance from the extracted emphysema region in a superimposed manner on the related bronchus or bronchi.

As a result, according to the second embodiment, the operator, such as a surgical operator, can recognize a responsible bronchus of the emphysema region to be diagnosed by a simple action of recognizing a single image in an axial cross section or a coronal cross section. The responsible bronchus is used herein to refer to a bronchus or a bronchus group that causes emphysema.

The operation of associating the emphysema region with the bronchus executed in step S103 is limited to neither a related bronchus group nor a responsible bronchus group. For example, branches which include terminals of a related bronchus group, such as lobe bronchi and subsegmental bronchi, may be displayed on the display 30.

In this case, in conventional medical image processing apparatuses, tubular structures less than about 0.5 mm are not detected as bronchi in three-dimensional image data, and therefore these tubular structures are not displayed on the display 30.

However, in the second embodiment, associating an emphysema region with a bronchus makes it possible to highlight the bronchus (group) within the range of a prescribed distance, so that more precise diagnosis can be performed.

Although some of the embodiments of the present invention have been described in the foregoing, the embodiments are merely illustrative and are not intended to restrict the scope of the invention. These new embodiments can be performed in other various forms, and various kinds of removals, replacements and modifications are possible without departing from the meaning of the present invention. These embodiments and their modifications are not only intended to be embraced in the range and scope of the invention but are also intended to be embraced in the invention set forth by the appended claims and in the equivalency thereof.

What is claimed is:

1. A medical image processing apparatus, comprising:
processing circuitry configured to
   extract an emphysema region that is at least part of a lung from three-dimensional image data,
   extract bronchi in the extracted emphysema region,
   calculate area ratios, each area ratio being between a lumen and a wall of each of the extracted bronchi, and
   identify a responsible bronchus that is within a prescribed distance from the emphysema region from among the bronchi,
   select an area ratio, corresponding to the responsible bronchus, from among the area ratios,
   allocate pixel values, corresponding to the selected area ratio, to corresponding positions on a bronchus image indicating the responsible bronchus so as to generate a superimposed image in which an area ratio image indicating the selected area ratio is superimposed on the bronchus image; and
   cause a display to display the superimposed image.

2. The medical image processing apparatus according to claim 1, wherein the processing circuitry is further configured to extract the emphysema region having a size larger than a prescribed size.

3. The medical image processing apparatus according to claim 1, wherein the processing circuitry is further configured to
   set the pixel values in a gradient of colors, and
   generate the superimposed image based on the area ratio image in the gradient of colors.

4. The medical image processing apparatus according to claim 1, wherein the processing circuitry is further configured to
   extract a core line of the responsible bronchus, and
   superimpose the area ratio image on the bronchus image related to a cross section orthogonal to the core line.

5. The medical image processing apparatus according to claim 1, wherein the processing circuitry is further configured to
   extract a core line of the responsible bronchus,
   determine contours of an inner wall and an outer wall of the responsible bronchus along the core line, and
   calculate, based on the determined contours of the inner wall and the outer wall, ratios between an area inside the contour of the outer wall of the responsible bronchus and an area obtained by excluding the area inside the contour of the inner wall from the area inside the contour of the outer wall, as the area ratios.

6. The medical image processing apparatus according to claim 3, wherein the processing circuitry is further configured to superimpose the area ratio image on the bronchus image in an axial cross section.

7. The medical image processing apparatus according to claim 1, wherein the processing circuitry is further configured to superimpose the area ratio image on the bronchus image in a sagittal cross section.

8. The medical image processing apparatus according to claim 1, wherein the processing circuitry is further configured to set the pixel values such that the area ratio image has transparency.

9. An image display control method for a medical image processing apparatus, comprising:
- extracting an emphysema region that is at least part of a lung, from three-dimensional image data;
- extracting bronchi in the extracted emphysema region;
- calculating area ratios, each area ratio being between a lumen and a wall of each of the extracted bronchi,
- identifying a responsible bronchus that is within a prescribed distance from the emphysema region from among the bronchi,
- selecting an area ratio, corresponding to the responsible bronchus, from among the area ratios;
- allocating pixel values, corresponding to the selected area ratio, to corresponding positions on a bronchus image indicating the responsible bronchus so as to generate a superimposed image in which an area ratio image indicating the selected area ratio is superimposed on the bronchus image; and
- displaying the superimposed image on a display.

* * * * *